(12) United States Patent
Pamukcu et al.

(10) Patent No.: US 6,369,092 B1
(45) Date of Patent: Apr. 9, 2002

(54) METHOD FOR TREATING NEOPLASIA BY EXPOSURE TO SUBSTITUTED BENZIMIDAZOLE DERIVATIVES

(75) Inventors: Rifat Pamukcu, Spring House; Gary A. Piazza, Doylestown, both of PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/845,501

(22) Filed: Apr. 30, 2001

Related U.S. Application Data

(63) Continuation of application No. 09/199,080, filed on Nov. 23, 1998.

(51) Int. Cl.7 .............................................. A61K 31/415
(52) U.S. Cl. ........................................ 514/394; 514/395
(58) Field of Search ................................ 514/395, 394

(56) References Cited

U.S. PATENT DOCUMENTS

| | | | |
|---|---|---|---|
| 3,031,450 A | 4/1962 | Fischer et al. ............... 514/260 |
| 3,161,654 A | 12/1964 | Shen .......................... 514/260 |
| 3,322,755 A | 5/1967 | Roch et al. .................. 514/260 |
| 3,517,005 A | 6/1970 | Cronin et al. ............... 514/260 |
| 3,594,480 A | 7/1971 | Cronin et al. ............... 514/260 |
| 3,647,858 A | 3/1972 | Hinkley et al. ............. 514/260 |
| 3,654,349 A | 4/1972 | Shen et al. .................. 514/260 |
| 3,780,040 A | 12/1973 | Schnettler et al. .......... 514/260 |
| 3,812,127 A | 5/1974 | Cronin et al. ............... 514/260 |
| 3,819,631 A | 6/1974 | Broughton et al. .......... 514/260 |
| 3,865,840 A | 2/1975 | Carson ....................... 514/260 |
| 3,920,636 A | 11/1975 | Takahasi et al. ............ 514/394 |
| 4,001,237 A | 1/1977 | Partyka et al. ............. 514/394 |
| 4,001,238 A | 1/1977 | Partyka et al. ............. 514/395 |
| 4,039,544 A | 8/1977 | Broughton et al. .......... 514/390 |
| 4,060,615 A | 11/1977 | Matier et al. ............... 514/395 |
| 4,076,711 A | 2/1978 | Ganguly et al. ............. 514/262 |
| 4,079,057 A | 3/1978 | Juby et al. .................. 514/265 |
| 4,098,788 A | 7/1978 | Crenshaw et al. .......... 514/265 |
| 4,101,548 A | 7/1978 | Crenshaw et al. .......... 514/390 |
| 4,102,885 A | 7/1978 | Crenshaw et al. .......... 514/390 |
| 4,138,561 A | 2/1979 | Crenshaw et al. .......... 514/390 |
| 4,146,718 A | 3/1979 | Jenks et al. ................. 514/390 |
| 4,161,595 A | 7/1979 | Kaplan et al. ............... 514/390 |
| 4,171,363 A | 10/1979 | Crenshaw et al. .......... 514/390 |
| 4,208,521 A | 6/1980 | Crenshaw et al. .......... 514/390 |
| 4,209,623 A | 6/1980 | Juby .......................... 514/394 |
| 4,423,075 A | 12/1983 | Dvornik et al. ............. 514/394 |
| 4,457,927 A | 7/1984 | Biere et al. ................. 514/310 |
| 4,460,590 A | 7/1984 | Möller ....................... 514/261 |
| 4,460,591 A | 7/1984 | DeGraw et al. ............ 514/310 |
| 4,880,810 A | 11/1989 | Lowe, III et al. ........... 514/310 |
| 4,885,301 A | 12/1989 | Coates ........................ 514/395 |
| 4,923,874 A | 5/1990 | McMahon et al. .......... 514/394 |
| 4,971,972 A | 11/1990 | Doll et al. ................... 514/310 |
| 5,073,559 A | 12/1991 | Coates ........................ 514/310 |
| 5,091,431 A | 2/1992 | Tulshian et al. ............. 514/394 |
| 5,147,875 A | 9/1992 | Coates et al. ............... 514/394 |
| 5,175,151 A | 12/1992 | Afonso et al. ............... 514/394 |
| 5,223,501 A | 6/1993 | Chakravarty et al. ....... 514/394 |
| 5,250,535 A | 10/1993 | Verheyden et al. ......... 514/394 |
| 5,254,571 A | 10/1993 | Coates et al. ............... 514/394 |
| 5,358,952 A | 10/1994 | Moschel et al. ............ 514/394 |
| 5,376,683 A | 12/1994 | Klar et al. ................... 514/390 |
| 5,393,755 A | 2/1995 | Neustadt et al. ............ 514/390 |
| 5,401,774 A | 3/1995 | Pamukcu et al. ............ 514/390 |
| 5,439,895 A | 8/1995 | Lee et al. .................... 514/390 |
| 5,488,055 A | 1/1996 | Kumar et al. ............... 514/390 |
| 5,614,530 A | 3/1997 | Kumar et al. ............... 514/395 |
| 5,614,627 A | 3/1997 | Takase et al. ............... 514/310 |
| 5,696,159 A | 12/1997 | Gross et al. ................. 514/315 |
| 5,728,563 A | 3/1998 | Tanaka et al. .............. 514/395 |
| 5,756,818 A | 5/1998 | Buchmann et al. ......... 514/395 |
| 5,852,035 A | 12/1998 | Pamukcu et al. ........... 514/394 |
| 5,858,694 A | 1/1999 | Piazza et al. ................ 514/395 |
| 5,874,440 A | 2/1999 | Pamukcu et al. ........... 514/394 |

FOREIGN PATENT DOCUMENTS

| | | |
|---|---|---|
| DE | 3038166 | of 1981 |
| DE | 274218 | 12/1989 |
| EP | 0 330 004 A1 | 6/1989 |
| EP | 0347146 A2 | 12/1989 |
| EP | 0349239 A2 | 1/1990 |
| EP | 0351058 | 1/1990 |
| EP | 0352960 A2 | 1/1990 |
| EP | 0395328 A2 | 10/1990 |
| EP | 0428268 A2 | 5/1991 |
| EP | 0463756 A1 | 1/1992 |
| EP | 0508586 A1 | 10/1992 |
| EP | 0526004 A1 | 2/1993 |
| EP | 0607439 A1 | 7/1994 |
| EP | 0722937 A1 | 7/1996 |
| EP | 0743304 A1 | 7/1996 |
| GB | 807826 | 1/1959 |
| GB | 2063249 A | 6/1981 |
| JP | 56-53659 A | 5/1981 |
| JP | 57-167974 A | 10/1982 |
| JP | 8-311035 | 11/1996 |
| WO | WO 92/03419 | 3/1992 |
| WO | WO 93/07149 | 4/1993 |
| WO | WO 93/12095 | 6/1993 |
| WO | WO 94/05661 | 3/1994 |

(List continued on next page.)

OTHER PUBLICATIONS

Waddell, W.R. et al., Am. J. Surgery, vol. 157, pp. 175–179 (1989).
Gonzaga, R.A.F. et al., The Lancet, Mar. 30, 1985, p. 751.
Waddell, W.R. et al., J. Surg. Oncology, vol. 24, pp. 83–87 (1983).
Federation Proceedings (1972) of the Federation of American Societies for Experimental Biology abstract Nos. 2044 and 2045.

(List continued on next page.)

Primary Examiner—Dwayne C. Jones
(74) Attorney, Agent, or Firm—Robert W. Stevenson

(57) ABSTRACT

A method for inhibiting neoplastic cells and related conditions by exposing them to substituted benzimidalole derivatives.

3 Claims, No Drawings

FOREIGN PATENT DOCUMENTS

| | | |
|---|---|---|
| WO | WO 94/19351 | 9/1994 |
| WO | WO 94/29277 | 12/1994 |
| WO | WO 95 18969 A | 7/1995 |
| WO | WO 95/26743 | 10/1995 |
| WO | WO 97/03070 | 1/1997 |
| WO | WO 97/03985 | 2/1997 |
| WO | WO 97/24334 | 7/1997 |
| WO | WO 98/14448 | 4/1998 |
| WO | WO 98/15530 | 4/1998 |
| WO | WO 98/16224 | 4/1998 |
| WO | WO 98/16521 | 4/1998 |
| WO | WO 98/17668 | 4/1998 |
| WO | WO 98/08848 | 5/1998 |
| WO | WO 98/23597 | 6/1998 |
| WO | WO 98/38168 | 9/1998 |
| WO | WO 96/32379 | 10/1998 |
| WO | WO 00/15222 | 3/2000 |

OTHER PUBLICATIONS

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effect of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelet, Biochem. Pharmacology, vol. 35, No. 5, pp 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol, vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine ",5" –Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l Cancer Inst., vol. 80, No. 2, pp. 90–96 (1988).

Lichtner, R. B. et al., The Pyrimido–pyrimidine Derivatives RA 223 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggregation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Ho–Sam Ahn et al., Potent Tetracyclic Guanine Inhibitors of PDE1 and PDE5 Cyclic Guanosine Monophosphate Phosphodiesterases with Oral Antihypertensive Activity; J. Med. Chem. 1997, 40, pp. 2196–2210.

J.A. Mitchell et al., Selectively of nonsteroidal antiinflammatory drugs as inhibitors of constitutive and inducible cyclooxygenase; Proc. Natl. Acad. Sci. USA, vol. 90, Dec. 1994, pp. 11693–11697.

J.D. Gaffen et al.: Increased killing of malignant cells by giving indomethacin with methotrexate, p. 30; col. 1; XP002084860Chemical Abstract, vol. 106, No. 11, Mar. 16, 1987, abstract No. 78377, J.D.

Tsou, K–C. et al. 5'–Nucleotide Phosphodiesterase Isozyme–V as a Marker for Liver Metastases in Breast Cancer Patients, Cancer 54:1788–1793, 1984.

Epstein, P M et al.; Dep. Pharmacol., Univ. Tex. Med. Sch., M.D. Anderson Hosp., Houston, Tex. 88030, USA Biosis 78:140912, Increased Cyclic Nucleotide Phospho Di Esterase Activity Associated With Proliferation and Cancer in Human and Murine Lymphoid Cells, 1993.

Christian Schudt et al., "Phosphodiesterase Inhibitors" The Handbook of Immunopharmacology, Academic Press, 1996, pp. 65–134.

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemia cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC Colon Carcinoma, Science, vol. 275, pp. 1784–1786, Mar. 21, 1997.

Mahmoud, N. et al., Apc Gene Mutation is Associated with a Dominant–Negative Effect upon intestinal Cell Migration, Cancer Research 57, pp. 5045–5050, Nov. 15, 1997.

Mahmoud, N. et al., Genotype–Phenotype Correlation in Murine Apc Mutation: Differences in Eterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

METHOD FOR TREATING NEOPLASIA BY EXPOSURE TO SUBSTITUTED BENZIMIDAZOLE DERIVATIVES

This application is Continuation of prior U.S. application Ser. No. 09/199,080 filed Nov. 23, 1998, entitled "Method for Treating Neoplasia by Exposure to Substituted Benzimidazole Derivatives," which is incorporated herein by reference.

TECHNICAL FIELD

This invention relates to compounds and methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical displasia (cervical cancer) and other such neoplasms.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because whatever cancer preventative (as opposed to cancer-fighting) capabilities those drugs may possess do not outweigh their severe side effects. Most standard chemotherapeutics are now believed to kill cancer cells by inducing apoptosis (also sometimes referred to as "programmed cell death"). Apoptosis naturally occurs in many tissues in the body. Apoptosis plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulcerations and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which causes gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans. Thus, the severe side effects due to induction of apoptosis in normal cells by conventional chemotherapeutics are avoided by these novel therapeutics (see, Van Stolk, et al., Gastroenterology. 112 (4): A673, 1997). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents potent compounds that induce apoptosis in neoplastic cells (but not substantially in normal cells), for treating patients with neoplastic lesions without substantially inhibiting PGE-2. This invention also involves methods for inducing such specific apoptosis in neoplastic cells by exposing such cells to a pharmacologically effective amount of those compounds described below to a patient in need of such treatment. Such compositions are effective in modulating apoptosis and modulating the growth of neoplasms, but are not suffering from the side effects of conventional chemotherapeutics and NSADDs.

DETAILED DESCRIPTION OF THE INVENTION

As discussed above, the present invention utilizes compounds of Formula I below

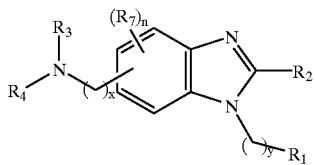

wherein $R_1$ is substituted or unsubstituted aryl, and wherein said aryl group is selected from the group consisting of phenyl, benzyl, pyridyl, dibenzofuranyl, naphthyl, quinolinyl and isoquinolinyl and wherein said substituents are one to three selected from the group consisting of halogen, lower alkyl, lower alkoxy, aryloxy, lower haloalkyl, CN, amino, nitro, phenyl;

$R_2$ is selected from a group consisting of hydrogen, halo-substituted or unsustituted lower alkyl, and lower alkoxy;

$R_3$ and R4 are independently selected from a group consisting of hydrogen, lower alkyl, —C(O)—$R_5$, —$CH_2$—$R_5$, or —$SO_2$—$R_5$;

$R_5$ is selected from a group consisting of halo-substituted or unsubstituted lower alkyl, lower alkoxy, $NHR_6$, lower alkenyl, and substituted or unsubstituted aryl, wherein said aryl group is selected from the group consisting of phenyl, benzyl, pyridyl, or pyridylmethyl, quinolinyl, thiazolyl, tetrazolyl, thiadiazolyl, and triazolyl and wherein said substituents are one to three independently selected from a group consisting of hydrogen, lower alkyl and lower alkoxy;

R6 is hydrogen or lower alkyl;

$R_7$ is selected from a group consisting of halogen, lower alkoxy, lower alkyl, lower alkoxycarbonyl, carboxyl, and carbamoyl; and x and y are 0, 1, or 2.

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

Also, the present invention is a method of inhibiting the growth of neoplastic cells by exposing the cells to an effective amount of compounds of Formula I, wherein $R_1$, $R_2$, $R_3$, $R_4$, $R_5$, $R_6$, $Ra_7$, m, n, x, and y are defined as above.

In still another form, the invention is a method of inducing apoptosis in human cells by exposing those cells to an effective amount of compounds of Formula I, wherein $R_1$ through $R_7$ m, n, x and y are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ through $R_7$ etc. are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

Compounds of this invention may be formulated into pharmaceutical compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.-

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

There are several general schemes for producing compounds useful in this invention.

Scheme I

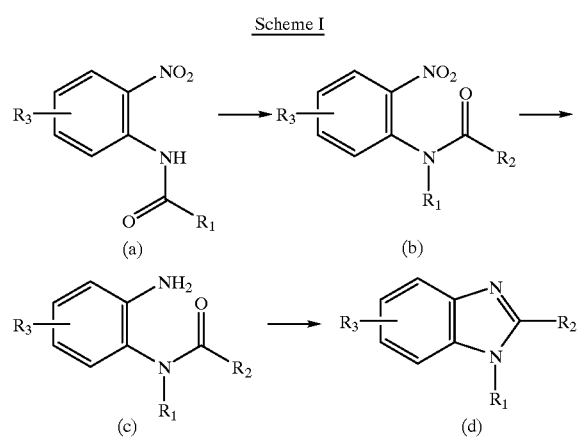

A substituted amide (a) is allowed to react with a base such as sodium hydride, lithium diisopropylamide. Reaction with a compound expressed by $R_2Z$ (Z represents a halogen atom or a sulfonyl chloride) gives the tertiary amide (b). There are several methods to obtain a compound of the formula (c). (A) Reduction with iron or zinc under an acidic condition, (B) reduction with a transition metal catalyst primarily exemplified by palladium, platinum, ruthenium, and nickel under a hydrogen environment, (C) reduction with a transition metal catalyst primarily exemplified by palladium, platinum, ruthenium, and nickel under a presence of formic acid, or (D) reduction with sodium hydrosulfite. In many cases when method (A) is used, a compound of the formula (c) is reduced within the reaction system to directly produce a compound of the formula (d). Some compounds may partially produce a compound of the formula (d) under any condition in the methods (A) through (D). A compound of the formula (d) is produced from a compound of the formula (c) with a carboxylic acid such as acetic acid, p-toluenesulfonic acid, hydrochloric acid, sulfuric acid, or phosphoric acid, sulfonic acid, or an inorganic acid.

Scheme II

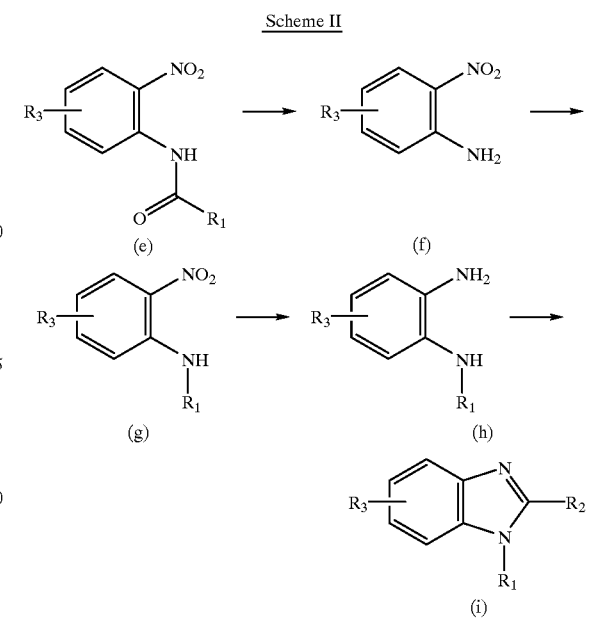

In scheme II, a compound of the formula (e) undergoes a hydrolysis or solvolysis with a base such as lithium bicarbonate, lithium carbonate, lithium hydroxide, sodium bicarbonate, sodium carbonate, sodium hydroxide, potassium bicarbonate, potassium carbonate, or potassium hydroxide, a carboxylic acid such as acetic acid, p-toluenesulfonic acid, hydrochloric acid, sulfuric acid, or phosphoric acid, sulfonic acid, or an inorganic acid and produces a compound expressed by the formula (f). A compound of the formula (f) is processed with a base such as sodium hydride, lithium diisopropylamide, and is processed with a compound expressed by $R_{1b}Z$ (Z represents a halogen or sulfonyl chloride) in order to produce a compound of the formula (g). A compound of the formula (g) can be altered to a compound of the formula (h) by a method such as (A) reducing it with iron or zinc under an acidic condition, (B) reducing it with a transition metal catalyst primarily exemplified by palladium, platinum, ruthenium, and nickel under a hydrogen environment, (C) reducing it with a transition metal catalyst primarily exemplified by palladium, platinum, ruthenium, and nickel under a presence of formic acid, and (D) reducing it with sodium hydrosulfite. A compound of the formula (i) is produced from a compound of the formula (h) and a corresponding carboxylic acid, acid chloride, acid bromide, or acid anhydride.

Scheme III

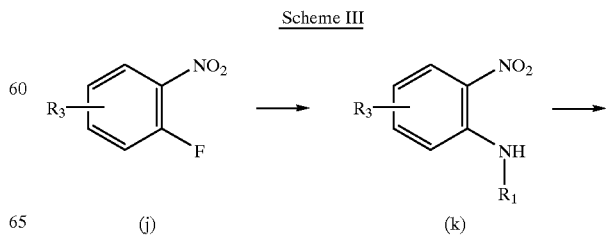

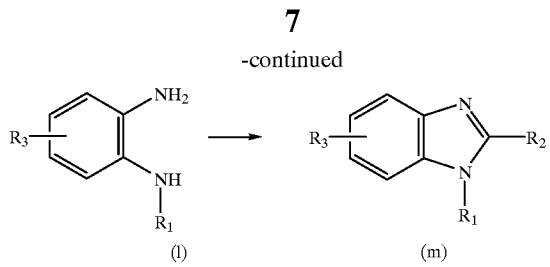

In scheme III, a compound of the formula (k) is produced from a compound of the formula (j) and a compound expressed by $R_1NH_2$. The alteration of a compound of the formula (k) to a compound of the formula (m) is the same as that of a compound of the formula (g) to a compound of the formula (i) in scheme II.

Scheme IV

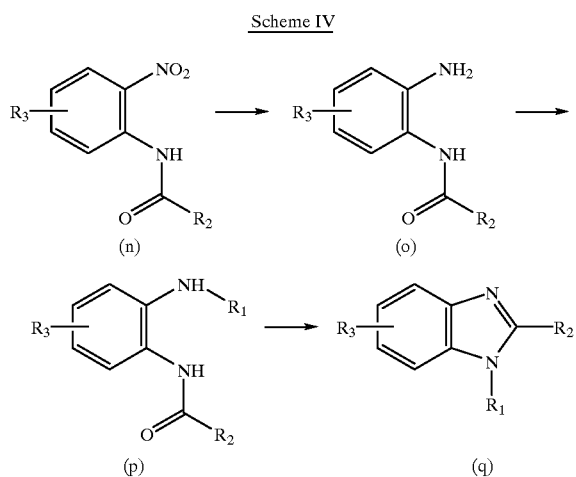

In scheme IV, a compound of the formula (n) can be altered to a compound of the formula (o) by a method such as (A) reducing it with a transition metal catalyst primarily exemplified by palladium, platinum, ruthenium, and nickel under a hydrogen environment, and (B) reducing it with sodium hydrosulfite. A compound of the formula (o) is processed with a base such as lithium hydrogencarbonate, lithium carbonate, lithium hydroxide, sodium hydrogencarbonate, sodium carbonate, sodium hydroxide, potassium hydrogencarbonate, potassium carbonate, or potassium hydroxide, and with a compound expressed by $R_1Z$ (Z represents a halogen atom, , or a sulfonyl chloride.) in order to produce a compound of the formula (p). A compound of the formula (q) is produced from a compound of the formula (p) with a carboxylic acid such as acetic acid, p-toluenesulfonic acid, hydrochloric acid, sulfuric acid, or phosphoric acid, sulfonic acid, or an inorganic acid.

Scheme V

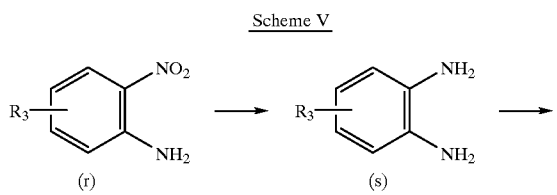

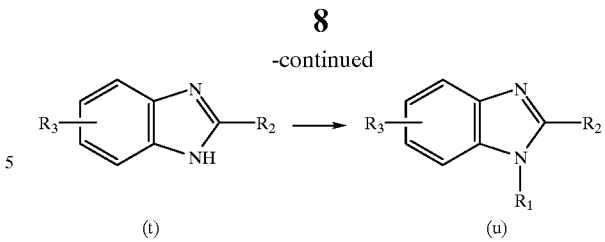

In scheme V, a compound of the formula (r) can be altered to a compound of the formula (s) by a method such as (A) reducing it with reduced iron or zinc under an acidic condition, (B) reducing it with a transition metal catalyst primarily exemplified by palladium, platinum, ruthenium, and nickel under a hydrogen environment, (C) reducing it with a transition metal catalyst primarily exemplified by palladium, platinum, ruthenium, and nickel under a presence of formic acid, and (D) reducing it with sodium hydrosulfite. A compound of the formula (t) is produced from a compound of the formula (s) and a corresponding carboxylic acid, acid anhydride, acid chloride, or acid bromide. A compound of the formula (t) is processed with a base such as sodium hydride or lithium diisopropylamide, and is processed with a compound expressed by $R_1Z$ (Z represents a halogen atom, or a sulfonyl chloride.) in order to produce a compound of the formula (u).

These methods usually produce a compound of the formula (u) having $R_3$ at mixed substitution positions of the fifth and sixth or of the fourth and seventh. The materials can be purified by a means such as recrystallization, column chromatography, thin film chromatography, or high speed liquid chromatography.

Scheme VI

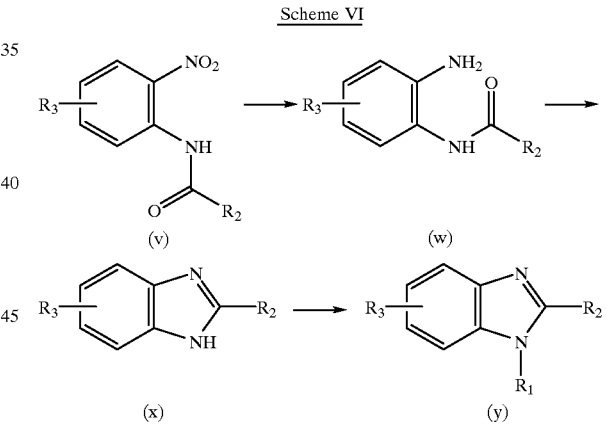

In scheme VI, a compound of the formula (v) can be altered to a compound of the formula (w) by a method such as (A) reducing it with reduced iron or zinc under an acidic condition, (B) reducing it with a transition metal catalyst primarily exemplified by palladium, platinum, ruthenium, and nickel under a hydrogen environment, (C) reducing it with a transition metal catalyst primarily exemplified by palladium, platinum, ruthenium, and nickel under a presence of formic acid, and (D) reducing it with sodium hydrosulfite. In many cases when the method (A) is used, a compound of the formula (w) forms a ring within the reaction system to directly produce a compound of the formula (x). Some compounds may partially produce a compound of the formula (x) under any condition in the methods (A) through (D). A compound of the formula (x) is produced from a compound of the formula (w) with a carboxylic acid such as acetic acid, p-toluenesulfonic acid, hydrochloric acid, sulfuric acid, or phosphoric acid, sulfonic acid, or an inorganic acid. A compound of the formula (x) can be altered to a benzimidazole compound by using the alteration method from the formula (t) to the formula (u) in scheme V. These methods usually produce a compound of the formula (y) having $R_3$ at mixed substitution positions of the fifth and sixth or of the fourth and seventh. The materials can be purified by a means such as recrystallization, column chromatography, thin film chromatography, or high speed liquid chromatography.

Scheme VII

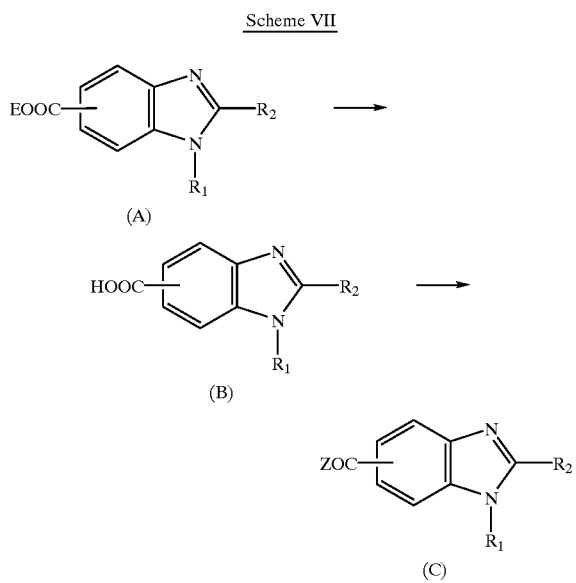

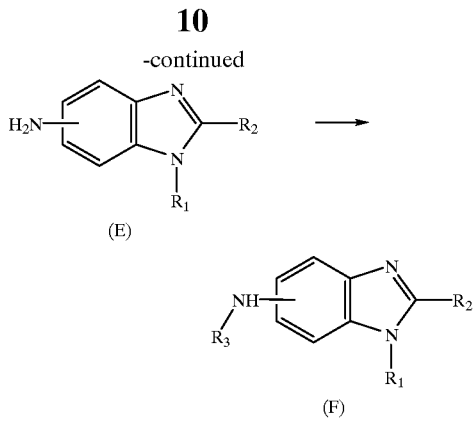

In scheme VIII, a compound of the formula (B) can be processed with an azide, primarily exemplified by diphenylphosporylazide, under a presence of an alcohol, primarily exemplified by t-butanol, to produce a compound of the formula (D). When a compound of the formula (D) is decomposed with an acid, a compound of the formula (E) is produced. A compound of the formula (F) is produced from a compound of the formula (E) and a compound expressed by $R_3Z$, wherein Z represents a halogen atom.

Scheme IX

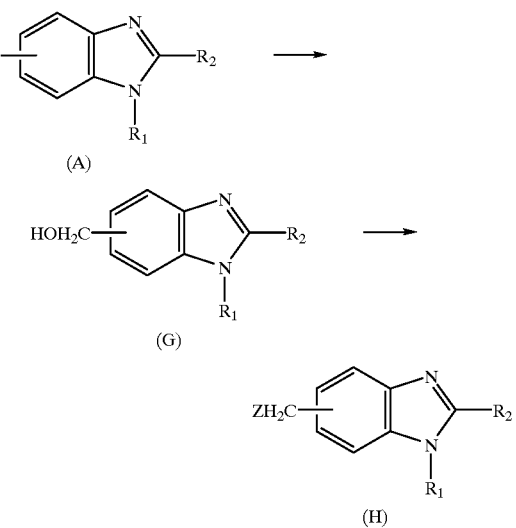

In scheme VII, a compound of the formula (A) undergoes a hydrolysis with a base such as lithium hydroxide, sodium hydroxide, and produces a compound of the formula (B). A compound of the formula (B) is processed with carbonyldiimidazole and then is processed with an amine or a sulfonamnide under a presence of a base to further produce benzimidazole derivatives.

A compound of the formula (B) can be altered to an acid halide expressed by the formula (C) by thionyl chloride, thionyl bromide, phosphorus trichloride, phosphorus pentachloride, or phosphorus oxychloride. Benzimidazole derivatives can be further produced by reacting a compound of the formula (C) with an amine or a sulfonamide.

Scheme VIII

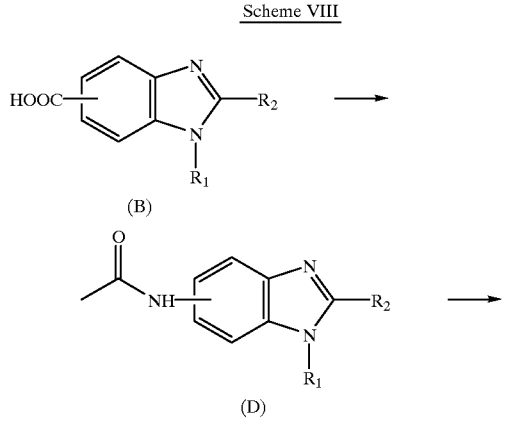

In schemeIX, a compound of the formula (A) can be altered by reduction to a compound of the formula (G). Furthermore, a compound of the formula (G) can be altered to a compound of the formula (H) by thionyl chloride, thionyl bromide, phosphorus oxychloride, phosphorus oxybromide, phosphorus trichloride, phosphorus pentachloride, methanesulfonyl chloride, or toluenesulfonyl chloride.

The foregoing may be better understood from the following examples that are presented for the purposes of illustration and are not intended to limit the scope of the invention. As used in the following examples, the references to substituents such as R1 Y, A, etc. refer to the corresponding substituents in Formula I above.

EXAMPLE I 6-t-Butoxycarbonylamino-1-(2-Chlorobenzyl)-2-n-Propylbenzimidazole

6-Carboxy-1-(2-chlorobenzyl)-2-n-propylbenzimidazole (200 mg) is suspended in t-butyl alcohol (5 ml), then diphenylphosphorylazide (0.19 ml) and diisopropylethylamine (0.21 ml) are added at room temperature. The reaction mixture is refluxed for 4 hours. Then, the solution is separated into layers using ethyl acetate and water. After the organic layer is washed with water and dried, it is concentrated under reduced pressure. The residue is developed and purified using column chromatography with ethyl acetate/hexane (1/10~1/3), recrystallized in ethyl acetate/hexane and 6-t-butoxycarbonyl-amino-1-(2-chlorobenzyl)-2-n-propylbenzinidazole (165 mg) is obtained. (Colorless crystals) $^1$H-NMR (CDCl$_3$, δ): 0.98 (3H, t, J=8 Hz), 1.50 (9H, s), 1.86 (2H, sextet, J=8 Hz), 2.72 (2H, t, J=8 Hz), 5.38 (2H, s), 6.40 (1H, dd, J=1, 8 Hz), 6.95 (1H, dd, J=1, 10 Hz), 7.08 (1H, dt, J=1, 8 Hz), 7.24 (1H, dt, J=1, 8 Hz), 7.28 (1H, d, J=1 Hz), 7.45 (1H, dd, J=1, 8 Hz), 7.66 (1H, d, J=10 Hz).

mp: 166–168° C.; ($R_1$=2-chlorobenzyl, $R_2$=2-n-propyl, $R_3$=—C(O)—$R_5$, $R_4$=H, $R_5$=t-butyl, n=0, x=0).

EXAMPLE 2

1-(2-Chlorobenzyl-6-Mesylamino-2-n-Propylbenzimidazole 1-(2-Chlorobenzyl)-2-n-propylbenzimidazole (150 mg) and triethylamine (61 mg) are dissolved in methylene chloride (3 ml). Methanesulfonyl chloride (70 mg) is added to the mixture solution at room temperature, stirred for 1 hour, and then washed with diluted hydrochloric acid. After it is washed with water, it is dried and the solvent is removed through evaporation under reduced pressure. The solid residue is filtered using ether, and 1-(2-chlorobenzyl)-6-mesylamino-2-n-propylbenzimidazole (124 mg) is obtained. $^1$H-NMR, (CDCl$_3$—CD$_3$OD, δ): 0.94 (3H, t, J=7.5 Hz), 1.76 (2H, m), 2.71 (2H, t, J=7.5 Hz), 2.81 (3H, s), 5.36 (2H, s), 6.40 (1H, d, J=7.5 Hz), 6.98–7.22 (4H,m), 7.40 (1H, d, J=7.5 Hz), 7.59 (1H, d, J=7.5 Hz).

mp: 191–193° C.; ($R_1$=2-chlorobenzyl, $R_2$=2-n-propyl, $R_3$=—SO$_2$—$R_5$, $R_4$=H, $R_5$=methyl, n=0, x=0).

EXAMPLE 3

6-Amino-1-(2-Chlorobenzyl)-2-n-Propylbenzimidazole 6-t-Butoxycarbonylamino-1-(2-chlorobenzyl)-2-n-propylbenzimidazole (700 mg) (example 1) is dissolved in a mixture solvent of methylene chloride (10 ml) and trifluoroacetic acid (1 ml), and the solution is stirred for five hours at room temperature. A small amount of methylene chloride is added into the reaction solution, and the solution is washed with sodium carbonate aqueous solution. After it is dried, the solvent is removed through evaporation. The residue is crystallized using a mixture solvent of normal hexane and ether, and 6-amino-1-(2-chlorobenzyl)-2-n-propylbenzimidazole (455 mg) is obtained. $^1$H-NMR (CDCl$_3$, δ): 1.01 (3H, t, J=7.5 Hz), 1.86 (2H, m), 2.73 (2H, t, J=7.5 Hz), 5.30 (2H, s), 6.41 (1H, d, J=1.5 Hz), 6.48 (1H, d, J=7.5 Hz), 6.66 (1H, dd, J=7.5 and 1.5 Hz), 7.10 (1H, t, J=7.5 Hz), 7.25 (1H, t, J=7.5 Hz), 7.46 (1H, d, J=7.5 Hz), 7.57 (1H, d, J=7.5 Hz).

mp: 121–122° C.; ($R_1$=2-chlorobenzyl, $R_2$=2-n-propyl, $R_3$=—H, $R_4$=H, n=0, x=0).

EXAMPLE 4

6-Acetylamino-1-(2-Chlorobenzyl)-2-n-Propylbenzimidazole

Acetic anhydride (62 mg) is added to a methylene chloride (3 ml) solution of 6-amino-1-(2-chlorobenzyl)-2-n-propylbenzimidazole (150 mg) (example 3) and triethylamine (61 mg) at room temperature, and the solution is stirred for one hour. After it is washed with water and dried, the solvent is removed through evaporation under reduced pressure. The residue is crystallized with ether, and 6-acetylamino-1-(2-chlorobenzyl)-2-n-propylbenzimidazole (143 mg) is obtained. $^1$H-NMR (CDCl$_3$, δ): 1.00 (3H, t, J=7.5 Hz), 1.86 (2H, m), 2.17 (3H, s), 2.73 (2H, t, J=7.5 Hz), 5.39 (2H, s), 6.43 (1H, d, J=7.5 Hz), 6.98–7.11 (2H, m), 7.22 (1H, t, J=7.5 Hz), 7.45 (1H, d, J=7.5 Hz), 7.59 (1H, brs), 7.68 (1H, d, J=7.5 Hz), 7.84 (1H, d, J=1.5 Hz).

mp: 180–182° C.; ($R_1$=2-chlorobenzyl, $R_2$=2-n-propyl, $R_3$=—C(O)—$R_5$, $R_4$=H, $R_5$=methyl, n=0, x=0).

EXAMPLE 5

1-(2-Chlorobenzyl)-2-n-Propyl-6-Ureidobenzimidazole

By using the same method as described in example 4, 1-(2-chlorobenzyl)-2-n-propyl-6-ureidobenzimidazole is produced. $^1$H-NMR (DMSO-d6, δ): 0.93 (3H, t, J=7.5 Hz), 1.72 (2H, m), 2.73 (2H, t, J=7.5 Hz), 5.43 (2H, s), 5.73 (2H, s), 6.42 (1H, dd, J=7.5 and 1.5 Hz), 7.05 (1H, dd, J=7.5 and 1.5 Hz), 7.22 (1H, dt, J=7.5 and 1.5 Hz), 7.33 (1H, dt, J=7.5 and 1.5 Hz), 7.45 (1H, d, J=7.5 Hz), 7.50 (1H, s), 7.57 (1H, dd, J=7.5 and 1.5 Hz), 8.50 (1H, s).

mp: 198° C.; ($R_1$=2-chlorobenzyl, $R_2$=2-n-propyl, $R_3$=—C(O)—$R_5$, $R_4$=H, $R_5$ NHR$_6$, $R_6$=H, n=0, x=0).

EXAMPLE 6

6-Benzenesulfonylaminomethyl-1-(2-Chlorobenzyl)-2-Methylbenzimidazole

A. 1-(2-Chlorobenzyl)-6-chloromethyl-2-methylbenzimidazole Hydrochloride

Thionyl chloride (5 ml) is added to 1-(2-chlorobenzyl)-6-chloromethyl-2-methylbenzimidazole (3.56 g), and the solution is stirred for 20 minutes at room temperature and then for 20 minutes at 80° C. After excess thionyl chloride is removed through evaporation under reduced pressure, the residue is dissolved in chloroform (10 ml), and crystallization is performed by adding hexane. The crystals are separated through filtration, washed in hexane, and dried. Thus, 1-(2-chlorobenzyl)-6-chloromethyl-2-methylbenzimidazole hydrochloride (4.07 g) is obtained. $^1$H-NMR (CDCl$_3$, δ): 3.01 (3H, s), 4.68 (2H, s), 5.61 (2H. s), 6.71 (1H, d, J=7.5 Hz), 7.24–7.29 (1H, m), 7.38 (1H, t, J=7.7 Hz), 7.44 (1H, s), 7.52 (2H, d, J=8.2 Hz), 7.92 (1H, d J=8.4 Hz).

B.) 6-Benzenesulfonylaminomethyl-1-(2-Chlorobenzyl)-2-Methylbenzimidazole

60% Sodium hydride (0.127 g) is added to an N,Ndimethylformamide (5 ml) solution of benzenesulfoamide (0.667 g) at room temperature, and the solution is stirred for one hour. Furthermore, 1-(2-chlorobenzyl)-6-chloromethyl-2-methylbenzimidazole hydrochloride (0.648 g) is added, and the solution is stirred for 18 hours at room temperature. Water is added to the solution and the reaction is halted. The solvent is removed under reduced pressure. Water and ethyl acetate are added to the residue and extraction is performed. An organic layer is concentrated and purification is performed through silica gel column chromatography (eluate: ethyl acetate), and thus, 6-benzenesulfonylaminomethyl-1-(2-chlorobenzyl)-2-methylbenzimidazole (0.240 g) is obtained. $^1$H-NMR (DMSO-d6, δ): 2.42 (3H, s), 4.02 (2H, m), 5.44 (2H, s), 6.36 (1H, d, J=7.7 Hz), 7.03 (1H, d, J=8.4 Hz), 7.18 (1H, s), 7.21 (1H, t), 7.33 (1H. t), 7.59–7.43 (5H, m), 7.73 (2H, d, J=7.5 Hz), 8.08 (1H, s).

IR:Br): 1522 cm$^{-1}$. mp: 164.5–167.0° C. ($R_1$=2-chlorobenzyl, $R_2$=methyl, $R_3$=—$SO_2$—$R_5$, $R_4$=H, $R_5$=phenyl, n=0, x=1).

EXAMPLE 7

1-(Biphenyl-4-ylmethyl)-2-Methyl-6-[(2-Pyridylmethyl)Aminomethyl]Benzimidazole

A.) 3-Acetylamino-4-nitro-ethylbenzoate

Acetyl chloride (9 ml) is added to a mixture of 3-amino-4-nitro-ethylbenzoate (18.4 g) and N,N-dimethylaniline (200 ml) under ice-chilled conditions, and the solution is stirred for 2 hours at room temperature. It is stirred for another 2 hours at 50° C. The reaction solution is poured into the cold 1N-hydrochloric acid, and then extraction is performed with ethyl acetate twice. After the organic layer is washed with 1N-hydrochloric acid, then with water, and dried, the solvent is removed through evaporation under reduced pressure. The residue is purified using silica gel column chromatography (eluate: ethyl acetate/hexane=1/10~1/4) and thus, 3-acetylamino-4-nitro-ethylbenzoate (19.6 g) is obtained. $^1$H-NMR (CDCl$_3$, δ): 1.42 (3H, t, J=7.1 Hz), 2.32 (3H, s), 4.43 (2H, q, J=7.1 Hz), 7.82 (1H, dd, J=1.8 and 8.7 Hz), 8.25 (1H, d, J=8.7 Hz), 9.35 (1H, d, J=1.8 Hz), 10.19 (1H, s).

B.) 1-(Biphenyl-4-ylmethyl)-6-ethoxycarbonyl-2-methylbenzimidazole

60% Sodium hydride (0.406 g) is added to an N,N-dimethylformamide (12 ml) solution of 3-acetylamino-4-nitro-ethylbenzoate (1.51 g) in an ice bath, and the solution is stirred for 40 minutes at room temperature. Then an N,N-dimethylformamide (10 ml) solution of 4-chloromethylbiphenyl (1.46 g) is added and the solution is stirred for three hours at room temperature. The reaction mixture is poured into cold 1N-hydrochloric acid, then extraction is performed using ethyl acetate twice. The organic layer is washed with 1N-hydrochloric acid, and then with water. After the solution is dried, the solvent is removed through evaporation under reduced pressure. The residue is purified using silica gel column chromatography (eluate: ethyl acetate/hexane=1/10~1/4), and oily of 3-[N-(biphenyl-4-ylnethyl)acetylamino]4-nitro-ethylbenzoate (1.44 g) is obtained. Ethanol (20 ml), acetic acid (11 ml), and reduced iron (3.07 g) are added into 3-[N-(2-chlorobenzyl)acetylamino]-4-nitro-ethylbenzoate (2.07 g), and the solution is refluxed for four hours. Solid are separated through filtration, and washed with ethanol. After the filtrate is concentrated, a sodium bicarbonate aqueous solution is added to the residue, and extraction is performed with ethyl acetate. After it is dried, the solvent is removed through evaporation under reduced pressure. The residue is purified using silica gel column chromatography (eluate: hexanelethyl acetate=100/0~70/30) and thus, 1-(biphenyl-4-ylmethyl)-6-ethoxycarbonyl-2-methylbenzimidazole (1.13 g) is obtained. $^1$H-NMR (CDCl$_3$, δ): 1.39 (3H, t, J=7.1 Hz), 2.62 (3H, s), 4.38 (2H, q, J=7.1 Hz), 5.42 (2H, s), 7.11 (2H, d, J=8.2 Hz), 7.34 (1H, m), 7.42 (2H, m), 7.54 (4H, m), 7.74 (1H, d, J=8.4 Hz), 7.99 (1H, dd, J=1.5 and 8.4 Hz), 8.06 (1H, d, J=1.5 Hz).

C.) 1-(Biphenyl-4-ylmethyl)-6-hydroxymethyl-2-methylbenzimidazole

Tetrahydrofuran (20 ml) solution of 1-(biphenyl-4-ylmethyl)-6-ethoxycarbonyl-2-methylbenzimidazole (5.30 g) is slowly added to a tetrahydrofuran (20 ml) solution of aluminum lithium hydride (2.17 g). Further, the solution is stirred for one hour at room temperature. By adding tetrahydrofuran (30 ml), the reaction solution is diluted. By adding a saturated sodium sulfate aqueous solution, the aluminum lithium hydride is decomposed, solidified and the tetrahydrofuran layer is separated. The solvent is removed through evaporation. Purification using silica gel column chromatography produced 1-(biphenyl-4-ylmethyl)-6-hydroxymethyl-2-methylbenzimidazole (3.72 g). $^1$H-NMR (CDCl$_3$, δ): 2.59 (3H, s), 4.78 (2H, s), 5.37 (2H. s), 7.11 (2H, d, J=8.3 Hz), 7.24 (1H, d, J=8.3 Hz), 7.30–7.37 (2H, m), 7.42 (2H, t), 7.51–7.56 (4H, m), 7.70 (1H, d, J=8.2 Hz).

D.) 1-(Biphenyl-4-ylmethyl)-6-chloromethyl-2-methylbenzimidazole

Thionyl chloride (2 ml) is added to a chloroform solution (30 ml) of 1-(biphenyl-4-ylmethyl)-6-hydroxymethyl-2-methylbenzimidazole (3.62 g), and the solution is stirred for one hour at 60° C. A sodium bicarbonate aqueous solution is added and the reaction is halted. The chloroform layer is washed with water and dried. After removing the solvent through evaporation under reduced pressure, ethyl acetate is added and crystallization is performed. After the crystals are separated through filtration and washed with ethyl acetate, they are dried and thus, 1-(biphenyl-4-ylmethyl)-6-chloromethyl-2-methylbenzimidazole (2.04 g) is obtained. $^1$H-NMR (CDCl$_3$, δ): 2.67 (3H, s), 4.71 (2H, s), 5.40 (2H. s), 7.12 (2H, d, J=8.2 Hz), 7.31–7.38 (3H, m), 7.43 (3, s), 7.52–7.58 (4H, m), 7.75 (1H, d, J=8.2 Hz).

E.) 1-(Biphenyl-4-ylmethyl)-2-methyl-6-[(2-pyridylmethyl)aminomethyl]benzimidazole To an N,N-dimethylformamide (3 ml) solution of 1-(biphenyl-4-ylmethyl)-6-chloromethyl-2-methylbenzimidazole (0.597 g) and potassium carbonate (0.350 g), 2-aminomethylpyridine (0.372 g) is added and the solution is stirred for two hours at 60° C. Water and ethyl acetate are added and extraction is performed. An organic layer is washed with water (twice). The solvent is removed under reduced pressure and a residue is obtained. The residue is purified through silica gel column chromatography (eluate: chloroform/methanol=9/1). Recrystallization is performed in a mixture solvent of ethyl acetate and hexane and thus, 1-(biphenyl4-ylmethyl)-2-methyl-6-[(2-pyridylmethyl) aminomethyl]benzimidazole 0.300 g is obtained. $^1$H-NMR (CDCl$_3$, δ): 2.57 (3H, s), 3.91 (2H, s), 3.93 (2H, s), 5.35 (2H, s), 7.08–7.14 (3H, m), 7.23 (2H, d, J=7.3 Hz), 7.30–7.35 (2H, m) 7.41 (2H, t), 7.50–7.55 (4H, m), 7.57 (1H, dt, J=1.8 and 7.6 Hz), 7.68 (1H, d, J=8.1 Hz), 8.53 (1H, d, J=4.9 Hz).

IR(KBr): 1618 cm$^{-1}$. mp: 104.5–106.0° C. ($R_1$=4-biphenyl, $R_2$=methyl, $R_3$=—$CH_2$—$R_5$, $R_4$=H, $R_5$=pyridyl, n=0, x=1).

EXAMPLE 8

6-t-Butoxycarbonylamino-1-(2-Chlorobenzyl)-2-Methylbenzimidazole

A.) 3-Amino-2-nitro-ethylbenzoate

A mixture of 3-acetylamino-2-nitro-benzoic acid (20.2 g), 97% sulfuric acid (11.4 g), and ethanol (300 ml) is stirred for 23 hours as it is refluxed by heating. Under reduced pressure, 100 ml of ethanol is removed through evaporation. After the solution is cooled down to room temperature, the reaction solution is poured into ice water (200 ml) containing sodium bicarbonate. Precipitated crystals are separated through filtration and washed with water. Furthermore, the crystals are dispersed in a 1 to 2 mixture solution (30 ml) of ethyl acetate and hexane. The crystals are then separated through filtration, washed with hexane, and subsequently dried to give 3-amino-2-nitro-ethylbenzoate (18.0 g). $^1$H-NMR (CDCl$_3$, δ): 1.39 (3H, t, J=7.1 Hz), 4.37 (2H, q, J=7.1 Hz), 6.41 (2H, br s), 6.83 (1H, d, J=8.7 Hz), 8.00 (1H, dd, J=1.8 and 8.7 Hz), 8.85 (1H, d, J=1.8 Hz).

B.) 3-Acetylamino-2-nitro-ethylbenzoate

Acetyl chloride (13 ml) is dripped into a solution of 3-amino-2-nitro-ethylbenzoate (2.98 g) and N,N-dimethylaniline (20 ml) in an ice bath. The solution is stirred for 48 hours at room temperature. The reaction solution is made acidic by adding 10% hydrochloric acid. Extraction is performed with ethyl acetate (twice), and the organic layer is washed with water (3 times). Under reduced pressure the solvent is removed and a residue is obtained. Crystals are formed from the residue by adding hexane. The crystals are separated through filtration, washed with hexane, dried, and thus, 3-acetylamino-2-nitro-ethylbenzoate (3.30 g) is obtained. $^1$H-NMR (CDCl$_3$, δ): 1.42 (3H, t), 2.33 (3H, s), 4.42 (2H, q), 8.27 (1H, dd, J=1.9 and 8.9 Hz), 8.89 (1H, d, J=1.9 Hz), 8.91 (1H, d, J=8.9 Hz), 10.54 (1H, br s).

C.) 4-Acetylamino-3-amino-ethylbenzoate

Under a hydrogen environment, a mixture of 3-acetylamino-2-nitro-ethylbenzoate (149.4 g), 5% palladium/carbon (14.9 g), and ethanol (1500 ml) is stirred for 15 hours. Solids are separated through filtration, a residue is obtained by concentrating the filtrate. The obtained residue is dissolved with a small amount of ethanol, and diisopropyl ether is added. Precipitated crystals are separated through filtration, dried, and thus, 4-acetylamino-3-amino-ethylbenzoate (114.4 g) is obtained. $^1$H-NMR (DMSO-d6, δ): 1.27 (3H, t), 2.05 (3H, s), 4.23 (2H, q), 5.19 (2H, s), 7.13 (1H, d, J=8.2 Hz), 7.35 (1H, s), 7.47 (1H, d, J=8.2 Hz), 9.19 (1H, s).

D.) -(2-Chlorobenzyl)-6-ethoxycarbonyl-2-methylbenzimidazole

2-Chlorobenzyl bromide (100 g) is added to an ethanol (750 ml) solution of 4-acetylamino-3-amino-ethylbenzoate (86.0 g) and potassium carbonate (37.3 g), and the solution is stirred for 14 hours at 60° C. Solids are separated through filtration and the filtrate is concentrated under reduced pressure. 35% hydrochloric acid (38.7 g) is added and the solution is stirred for two hours at 60° C. After solids are separated through filtration and the solution is neutralized with sodium bicarbonate, the ethanol is removed through evaporation under reduced pressure. Ethyl acetate and water are added, and extraction is performed (three times). After the organic layer is washed with water and dried, the solvent is removed through evaporation until the organic layer became. Precipitated crystals are separated through filtration and are recrystallized through ethanol. Thus, 1-(2-chlorobenzyl)-6-ethoxycarbonyl-2-methylbenzimidazole (54.3 g) is obtained. Furthermore, crystals are obtained by collecting and concentrating all filtrates. The crystals are recrystallized with ethanol. Thus, 1-(2-chlorobenzyl)-6-ethoxycarbonyl-2-methylbenzimidazole (18.1 g) is obtained. $^1$H-NMR (CDCl$_3$, δ): 1.39 (3H, t, J=7.1 Hz), 2.57 (3H, s), 4.37 (2H, q, J=7.1 Hz), 5.46 (2H, s), 6.41 (1H. d, J=7.8 Hz), 7.10 (1H, t, J=7.8 Hz), 7.25 (1H, t), 7.47 (1H, d, J=8.0 Hz), 7.75 (1H, d, J=8.4 Hz), 7.94 (1H, s), 8.00 (1H, d,=1.5 and 8.4 Hz).

mp: 126.0–127.0° C.

E.) 6-Carboxy-1-(2-chlorobenzyl)-2-methylbenzimidazole

Ethanol (80 li) and 10% sodium hydroxide aqueous solution (37 g) are added to 1-(2-chlorobenzyl)-6-ethoxycarbonyl-2-methylbenzimidazole (10.0 g), and the solution is refluxed for 4 hours. After the reaction solution is cooled, its acidity is adjusted to pH 6 with 10% hydrochloric acid. The sediment is gathered, washed with water, dried under reduced pressure, and thus, 6-carboxy-1-(2-chlorobenzyl)-2-methylbenzimidazole (8.30 g) is obtained.

F.) $^6$-t-Butoxycarbonylamino-1-(2-chlorobenzyl)-2-methylbenzimidazole By using the method of example 1, 6-t-butoxycarbonylamino-1-(2-chlorobenzyl)-2-methylbenzimidazole (0.760 g) is obtained from 6-carboxy-1-(2-chlorobenzyl)-2-methylbenzimidazole (1.01 g), diphenylphosphorylazide (1 ml), diisopropylethylamine (1 ml), and t-butylalcohol (25 ml). $^1$H-NMR (CDCl$_3$, δ): 1.49 (9H, s), 2.47 (3H, s), 5.37 (2H, s), 6.41(1H, d, J=7.5 Hz), 6.55 (1H, br s), 6.93 (1H, dd, J=1.9 and 8.6 Hz), 7.08 (1H, t, J=7.5 Hz), 7.22 (1H, t), 7.44(1H, d, J=8.0 Hz), 7.62 (2H, d, J=8.6 Hz).

($R_1$=2-chlorobenzyl, $R_2$=methyl, $R_3$=—C(O)—$R_5$, $R_4$=H, $R_5$=t-butyl, n=0, x=0).

EXAMPLE 9

6-Amino-1-(2-Chlorobenzyl)-2-Methylbenzimidazole

By using the method of example 3, 6-amino-1-(2-chlorobenzyl)-2-methylbenzimidazole (0.420 g) is obtained from 6-t-butoxycarbonylamino-1-(2-chlorobenzyl)-2-methylbenzimidazole (0.760 g) (example 8). $^1$H-NMR (DMSO-d6, δ): 2.37 (3H, s), 4.83 (2H, br s), 5.32 (2H, s), 6.33 (1H, d, J=1.9 Hz), 6.42 (1H, d, J=7.7 Hz), 6.46 (1H, dd, J=1.9 and 8.5 Hz), 7.19–7.24 (2H, m), 7.31 (1H, t), 7.53 (1H, d, J=7.9 Hz).

($R_1$=2-chlorobenzyl, $R_2$=methyl, $R_3$=H, R=H, n=0, x=0).

EXAMPLE 10

6-(1-Butanesulfonylamino)-1-(2-Chlorobenzyl)-2-Methylbenzimidazole

By using the method of example 2, 6-(1-butanesulfonylamino)-1-(2-chlorobenzyl)-2-methylbenzimidazole (0.230 g) is obtained from 6-amino-1-(2-chlorobenzyl)-2-methylbenzimidazole (0.300 g) (example 9), 1-butanesulfonyl chloride (0.216 g), and triethylamine (0.130 g). $^1$H-NMR (DMSO-d6, δ): 0.74 (3H, m), 1.23 (2H, m), 1.55 (2H, m), 2.50 (3H, s), 2.89 (2H, m), 5.47 (2H, s), 6.58 (1H, d, J=7.4 Hz), 7.02 (1H, d, J=8.5 Hz), 7.10 (1H, s), 7.23 (1H, t), 7.33 (1H, t), 7.52 (2H, m), 9.55 (1, s) IR(KBr): 1629 cm$^{-1}$.

mp: 149.5–151.0° C.

($R_1$=2-chlorobenzyl, $R_2$=methyl, $R_3$=—SO$_2$—$R_5$, $R_4$=H, $R_5$=butyl, n=0, x=0).

The compounds of this invention can be formulated with pharmaceutically acceptable carriers into unit dosage forms in a conventional manner so that the patient in need of therapy for precancerous lesions can periodically (e.g., once or more per day) take a compound according to the methods of this invention. The exact initial dose of the compounds of this invention can be determined with reasonable experimentation. One skilled in the art should understand that the initial dosage should be sufficient to achieve a blood plasma concentration approaching a percentage of the IC$_{50}$ value of the compound, with the percentage depending on the chemopreventative or chemotherapeutic indication. The initial dosage calculation would also take into consideration several factors, such as the formulation and mode of administration, e.g. oral or intravenous, of the particular compound. For example, assuming a patient with an average circulatory system volume of about four liters, based on the IC$_{50}$ values for compounds of this invention, one would calculate a dosage of from about 1–400 mg of such compounds for intravenous administration to achieve a systemic circulatory concentration equivalent to the IC$_{50}$ concentration.

It will be understood that various changes and modifications can be made in the details of procedure, formulation and use without departing from the spirit of the invention, especially as defined in the following claims.

We claim:

1. A method for inhibiting the growth of neoplastic cells comprising exposing the cells to a growth inhibiting effective amount of a compound of Formula I:

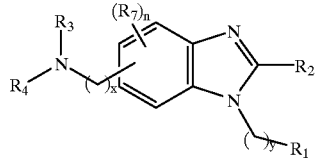

wherein
- $R_1$ is substituted or unsubstituted aryl, and wherein said aryl group is selected from the group consisting of phenyl, benzyl, pyridyl, dibenzofuranyl, naphthyl, quinolinyl and isoquinolinyl and wherein said substituents are one to three selected from the group consisting of halogen, lower alkyl, lower alkoxy, aryloxy, lower haloalkyl, CN, amino, nitro, phenyl;
- $R_2$ is selected from a group consisting of hydrogen, halo-substituted or unsustituted lower alkyl, and lower alkoxy;
- $R_3$ and $R_4$ are independently selected from a group consisting of hydrogen, lower alkyl, —C(O)—$R_5$, —$CH_2$—$R_5$, or —$SO_2$—$R_5$;
- $R_5$ is selected from a group consisting of halo-substituted or unsubstituted lower alkyl, lower alkoxy, NHR6, lower alkenyl, and substituted or unsubstituted aryl, wherein said aryl group is selected from the group consisting of phenyl, benzyl, pyridyl, or pyridylmethyl, quinolinyl, thiazolyl, tetrazolyl, thiadiazolyl, and triazolyl, and wherein said substituents are one to three independently selected from a group consisting of hydrogen, lower alkyl and lower alkoxy;
- $R_6$ is hydrogen or lower alkyl;
- $R_7$ is selected from a group consisting of halogen, lower alkoxy, lower alkyl, lower alkoxycarbonyl, carboxyl, and carbamoyl; and
- x and y are 0, 1, or 2.

2. A method of treating a mammal having precancerous lesions comprising administering a pharmacologically effective amount of a compound of Formula I:

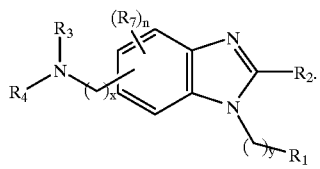

3. A method for regulating apoptosis in human cells comprising exposing said cells to an effective amount of a compound of the formula:

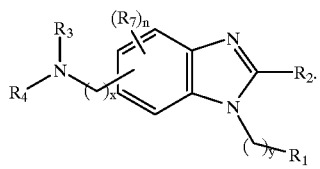

* * * * *